(12) United States Patent
Hino

(10) Patent No.: US 7,695,429 B2
(45) Date of Patent: Apr. 13, 2010

(54) ENDOSCOPE CONNECTOR DEVICE, ENDOSCOPE CABLE LEAD-OUT UNIT AND ENDOSCOPE DEVICE

(75) Inventor: Kazuhiko Hino, Saitama (JP)

(73) Assignee: Fujinon Corporation, Saitama-Shi (JP)

( * ) Notice: Subject to any disclaimer, the term of this patent is extended or adjusted under 35 U.S.C. 154(b) by 1360 days.

(21) Appl. No.: 11/134,429

(22) Filed: May 23, 2005

(65) Prior Publication Data

US 2005/0267333 A1 Dec. 1, 2005

(30) Foreign Application Priority Data

May 25, 2004 (JP) .............................. 2004-154480
Jul. 2, 2004 (JP) .............................. 2004-197332

(51) Int. Cl.
*A61B 1/00* (2006.01)
(52) U.S. Cl. ........................ 600/132; 600/109; 600/160
(58) Field of Classification Search ................ 600/101, 600/109, 110, 112, 113, 130–132, 160, 164, 600/178, 182
See application file for complete search history.

(56) References Cited

U.S. PATENT DOCUMENTS

| | | | | |
|---|---|---|---|---|
| 4,601,284 A | * | 7/1986 | Arakawa et al. ............. | 600/112 |
| 4,860,731 A | * | 8/1989 | Matsuura ..................... | 600/157 |
| 4,888,639 A | * | 12/1989 | Yabe et al. ..................... | 348/69 |
| 4,901,142 A | * | 2/1990 | Ikuno et al. ................... | 348/69 |
| 4,947,828 A | * | 8/1990 | Carpenter et al. ........... | 600/113 |
| 5,029,016 A | * | 7/1991 | Hiyama et al. .............. | 358/403 |
| 5,239,983 A | | 8/1993 | Katsurada | |
| 5,810,714 A | * | 9/1998 | Takamura et al. ........... | 600/134 |
| 5,888,191 A | * | 3/1999 | Akiba et al. ................. | 600/153 |
| 6,319,197 B1 | | 11/2001 | Tsuji et al. | |
| 6,443,888 B1 | | 9/2002 | Ogura et al. | |
| 6,520,908 B1 | * | 2/2003 | Ikeda et al. .................. | 600/132 |
| 2002/0013510 A1 | * | 1/2002 | Moriyama ................... | 600/118 |
| 2002/0188174 A1 | * | 12/2002 | Aizawa et al. .............. | 600/118 |
| 2003/0073955 A1 | * | 4/2003 | Otawara ................. | 604/164.01 |
| 2003/0149339 A1 | * | 8/2003 | Ishibiki ....................... | 600/160 |

FOREIGN PATENT DOCUMENTS

| | | |
|---|---|---|
| JP | 64-068711 | 3/1989 |
| JP | 01197714 A * | 8/1989 |
| JP | 04-125612 A | 4/1992 |
| JP | 5-228104 | 9/1993 |
| JP | 06-030897 A | 2/1994 |
| JP | 7-24653 | 3/1995 |
| JP | 10-211168 A | 8/1998 |
| JP | 11-337840 A | 12/1999 |
| JP | 2000-056238 A | 2/2000 |
| JP | 2000-225093 | 8/2000 |
| JP | 2003-235797 | 8/2003 |
| WO | WO 95/17845 | 7/1995 |

* cited by examiner

*Primary Examiner*—John P Leubecker
*Assistant Examiner*—Samuel Candler
(74) *Attorney, Agent, or Firm*—Birch, Stewart, Kolasch & Birch, LLP

(57) ABSTRACT

An endoscope connector device comprises: a first cable of an endoscope, including a light guide for supplying illumination light and an electric wire for obtaining video signals from an image pickup device; a light guide connector connected to the first cable; and a second cable of the endoscope, including the electric wire led out of the light guide connector, wherein the second cable is attached diagonally from the light guide connector at an angle θ within a range of 0°<θ<90° from a first cable side of an axial direction of the first cable.

2 Claims, 12 Drawing Sheets

SECOND CABLE SIDE

FIRST CABLE SIDE

ENDOSCOPE CONNECTOR DEVICE, ENDOSCOPE CABLE LEAD-OUT UNIT AND ENDOSCOPE DEVICE

RELATED APPLICATIONS

This application claims the priority of Japanese Patent Application Nos. 2004-154480 and 2004-197332, filed on May 25, 2004 and Jul. 2, 2004, respectively, which are incorporated herein by reference.

BACKGROUND OF THE INVENTION

1. Field of the Invention

The present invention relates to an endoscope connector device, more specifically, the construction of a connector device for connecting a light guide for supplying illumination light to a light source unit and connecting an electric wire for obtaining video signals to a processor unit.

The invention relates to an endoscope cable lead-out unit, more specifically, a construction of a cable lead-out part which is used for a portion where an endoscope cable including various linear members is branched, and branches an electric wire from a light guide connector for connection to a light source unit.

2. Description of the Related Art

FIG. 7 and FIG. 8 show the construction of the related-art endoscope (electronic endoscope), and FIG. 7 is described in Japanese Examined Patent Application No. H07-24653, and FIG. 8 is described in Japanese Published Unexamined Patent Application NO. 2000-225093.

The endoscope apparatus of FIG. 7 includes an endoscope 51, a light source unit 52 and an image pickup control unit 53 placed on the light source unit 52, and a universal cable 54a of the endoscope 51 including a light guide and a signal line, etc., is connected to a front panel 52A (operation switch and the like are arranged thereon) of the light source unit 52 by a light source part connector 54b, and a signal cable 54c attached to the side face of this connector 54b is connected to the front panel 53A of the image pickup control unit 53 by a connector 54d. The signal cable 54c can be removed from the light source part connector 54b by a connector 54e.

In the endoscope apparatus shown in FIG. 8, a light source unit 56 is placed on the processor unit 55, and to the front panel 56A (on which an operation switch, etc., are arranged) of the light source unit 56, an endoscope cable 57a including a light guide and an electric wire, etc., is connected by a connector part 57b, and a cable (electric cable) 57c attached to the lower side of the connector 57b is connected to the front panel 55A of the processor unit 55 by a connector 57a. Thus, in the related-art endoscope apparatus, a light guide and an electric wire (or a signal line) are installed inside one endoscope cable, and the light guide is connected to a light source unit 52 or 56 and the electric wire is connected to an image pickup control unit 53 or a processor unit 55.

In an endoscope (electronic endoscope) apparatus, a first cable including a light guide for supplying illumination light and an electric wire for obtaining video signals from an image pickup device is connected to a light source unit via a light guide connector, and a second cable of the endoscope which includes the electric wire extracted so as to be branched from the light guide connector is connected to a processor unit for video signal processing via an electric connector.

FIG. 18A and FIG. 18B show a construction example (employing a detachable connector type on the lead-out part of the electric wire) of the cable lead-out part of the light guide connector part, and in this light guide connector, a first cable (including a light guide and an electric wire 2) is laid from the endoscope distal end part, and a cylindrical lead-out part outer sheath 1b is integrally formed from a synthetic resin (hard) so as to project from the outer sheath 1a of the light guide connector main body. To the distal end side of this lead-out part outer sheath 1b, a metallic insert ring 1c is attached.

On the other hand, a pin supporting part 3a that connects the electric wire 2 guided from the light guide connector main body is installed inside a connector receiver 3b, and this connector receiver 3b is attached to the outer sheath 1b as shown in FIG. 18B by being fit to the inner surface of the insert ring 1c and fixed by screws 4 at a plurality of points. This connector receiver 3b is coupled to a connector inserting part to which the second cable is connected by a fixing ring 5, whereby the electric wire to the processor unit is linked.

However, the related-art endoscope connector devices have the following problems. Namely, in the endoscope apparatus of FIG. 7, as illustrated, the cable 54c to be attached to the light source part connector 54b is led out rightward along the front panel 52A, so that the cable 54c to be linked to the image pickup control unit 53 occupies the front of the front panels (operation panels) 52A and 53A of the light source unit 52 and the image pickup control unit 53, and remarkably disturbs various operations on the operation parts arranged on the front panels 52A and 53A. On the other hand, the cable 54c to be connected to the image pickup control unit 53 is made detachable by the connector 54e, however, when this is attached to or detached from the light source part connector 54b connected to the light source unit 52, the connector 54e is inserted or detached along (in parallel to) the front panel 52A at a position close to the front panel 52A of the light source unit 52, so that this detaching and attaching operation becomes difficult. In order to avoid this, it is also considered that the position of the connector 54e is separated far from the front panel 52A, however, this case lengthens the light source part connector 54b.

Furthermore, in the endoscope apparatus of FIG. 8, obstruction of access to the operation part of the front panel as described above is rare, however, the upper and lower cables 57a and 57c attached to the connector part 57b are adjacent to each other, so that cleaning between these cables 57a and 57c becomes difficult. In addition, the distance between the base end portion (connector part 57b side) of the cable (electric wire cable) arranged on the lower side and the connecting position of the connector 57d in the processor unit 55 is short, the cable 57c is bent at a small curvature, and this burdens a great load on the cable 57c.

Furthermore, in the case of FIG. 7, the cable 54c is arranged so as to be led out vertically to the right side from the light source part connector 54b, however, in the related art, in some cases, as shown in Japanese Published Unexamined Patent Application No. 2003-235797, opposite to the case of FIG. 7, the cable (corresponding to 54c) that extends to a signal processing unit is led out to the left side of the light guide connector (corresponding to 54b) also exists. In this case, disturbance of various operations on the front panels of the light source unit and the signal processing unit is reduced. However, in many endoscopes, it is required that the control portion (51A of FIG. 7) is held by the left hand and the light guide connector (light source part connector) is inserted into the light source unit by the right hand and then the cable and connector positioned on the left hand side are held and connected to the signal processing unit (processor unit), and this connection is troublesome. In addition, as described in FIG. 7, when the cable 54c is attachable to and detachable from the connector 54e, this connector 54e must be connected to the left side of the light source part connector 54b (light guide connector) by the right hand, and this connection is not easy.

In addition, in some the related-art cases, instead of attachment of the cables 54c and 57c toward the sides of the image pickup device control unit 53 and the processor unit 55 to the connectors 54b and 57b as shown in FIG. 7 and FIG. 8, an endoscope cable (54a or 57a) is branched into two of a light source side cable and a processor unit side cable at the middle of the cable as shown in Japanese Published Unexamined Patent Application No. H05-228104. However, in this case, the connectors of the two branched cables swing as pendulums, and the connectors themselves may be broken due to collision of these.

With the construction of the cable lead-out part of FIG. 18, since the insert ring 1c is arranged inside the outer sheath 1b made of a synthetic resin (plastic) and the connector receiver 3b is screw-tightened and fixed to this insert ring 1c, when the second cable is connected, a stress concentrates at the lead-out part outer sheath 1b around the insert ring 1c and may break the plastic-made outer sheath 1b. In addition, tightening and fixing of the plurality of screws (4) for connecting the connector receiver 3b are troublesome.

In order to avoid such breakage of the plastic-made lead-out part outer sheath 1b, it is considered that the lead-out part is reinforced by arranging a metallic supporter inside the lead-out part, however, in this case, it is necessary that the metallic supporter of the lead-out part is fixed to the metallic supporter or the like inside the light guide connector main body by some method, and this fixing method becomes complicated.

SUMMARY OF THE INVENTION

The invention was made in view of the above-described problems, and a first object thereof is to provide an endoscope connector device that is easy to be used and has advantages in that excellent access to the operation part can be secured by widening the front side space of the front panels of the light source unit or the processor unit, and makes cable connections to the light source unit and the processor unit easy, and cleaning performance is high.

The invention was made in view of the above-described problems, and a second object thereof is to provide an endoscope cable lead-out unit which can eliminate the possibility of breakage of the synthetic resin-including outer sheath, makes leading-out and assembling of the cable easy, and realizes a simple construction in the case where the cable is taken out from the main body.

In order to achieve the above-mentioned first object, according to a first aspect of the invention, there is provided an endoscope connector device comprising: a first cable of an endoscope, including a light guide for supplying illumination light and an electric wire for obtaining video signals from an image pickup device; a light guide connector connected to the first cable; and a second cable of the endoscope, including the electric wire led out of the light guide connector, wherein the second cable is attached diagonally from the light guide connector at an angle θ within a range of 0°<θ<90° from a first cable side of an axial direction of the first cable.

In addition, according to the invention, there is provided an endoscope device comprising: an endoscope connector device as described in the first aspect of the invention; a light source unit that connects the first cable via the light guide connector; and a video signal processor unit that connects the second cable via an electric connector; wherein the second cable is arranged on a right side of the light guide connector, the light guide connector being connected to the light source unit so as to face a front panel of the light source unit.

According to a second aspect of the invention, the light guide connector comprises an intermediate connector so as to make the second cable attachable to and detachable from the light guide connector.

According to a third aspect of the invention, when the processor unit is arranged below the light source unit, the second cable is attached so as to turn downward at an angle $\phi_a$ in a range of 0°<$\phi_a$<90° from its horizontal position at which the light guide connector is connected, and, when the processor unit is arranged above the light source unit, the second cable is attached so as to turn upward at an angle $\phi_b$ in a range of 0°<$\phi_b$<90° from its horizontal position at which the light guide connector is connected.

With the above-mentioned construction, the second cable is led out diagonally rearward at an angle θ of for example 45 degrees (or 30 through 60 degrees) with respect to the first cable and attached on the right side of the light guide connector in a state in that it faces the front panel of the light source unit when the light guide connector is connected, and in comparison with the case where the second cable is arranged in parallel to the front panel, the space in front of the front panel as an operation space becomes wider according to the diagonally rearward withdrawal.

Furthermore, with the construction according to the third aspect, in the layout in that the light source unit and the processor unit are stacked vertically, when the processor unit is placed below the light source unit, the second cable is attached downward at an angle φ of, for example, approximately 20 to 30 degrees from its horizontal position, and on the other hand, when the processor unit is placed above the light source unit, the second cable is attached upward at the angle φ of, for example, 20 to 30 degrees from its horizontal position.

In order to achieve the above-described second object, according to a fourth aspect of the invention, there is provided an endoscope cable lead-out unit for leading-out a cable from a main body, comprising: an outer sheath that includes a synthetic resin and is formed so as to project in a cable lead-out direction from the main body; a metallic lead-out part frame (supporting frame) for retaining and fixing a cable or components of the cable, arranged inside the outer sheath while engaging with a base end side of the outer sheath; and a presser ring that is screwed and coupled to the lead-out part frame and engages a the distal end side of the outer sheath in this screw-coupled state, wherein the outer sheath is nipped by the presser ring and the lead-out part frame.

According to a fifth aspect of the invention, the lead-out part frame comprises: a first frame adjacent to the main body; and a second frame that is detachably attached to the first frame by a latching unit and retains and fixes the cable or components of the cable, and the presser ring is arranged on the second frame.

According to a sixth aspect of the invention, the main body is a light guide connector that connects a first cable including: a light guide for illumination light supply; and an electric wire for video signal transmission to a light source unit, and the endoscope cable lead-out unit is applied to a lead-out part of the light guide connector from which a second cable for linking the electric wire from the light guide connector to a processor unit is led out diagonally rearward from the light guide connector that is connected to the light source unit while facing a front panel of the light source unit.

According to the construction of the fourth aspect, a metallic frame of the lead-out part independent from the metallic supporting member of the main body side is disposed inside the outer sheath, and the synthetic resin-including outer sheath is nipped by this frame and the presser ring, whereby the metallic frame that retains the cable or components thereof is easily attached inside the lead-out part outer sheath.

According to the construction of the fifth aspect, the synthetic resin-including outer sheath is nipped by the first frame and the presser ring on the side of the second frame, whereby the second frame that retains the cable or components thereof is easily attached inside the lead-out part outer sheath.

DETAILED DESCRIPTION OF THE INVENTION

First Embodiment

Figure 1:
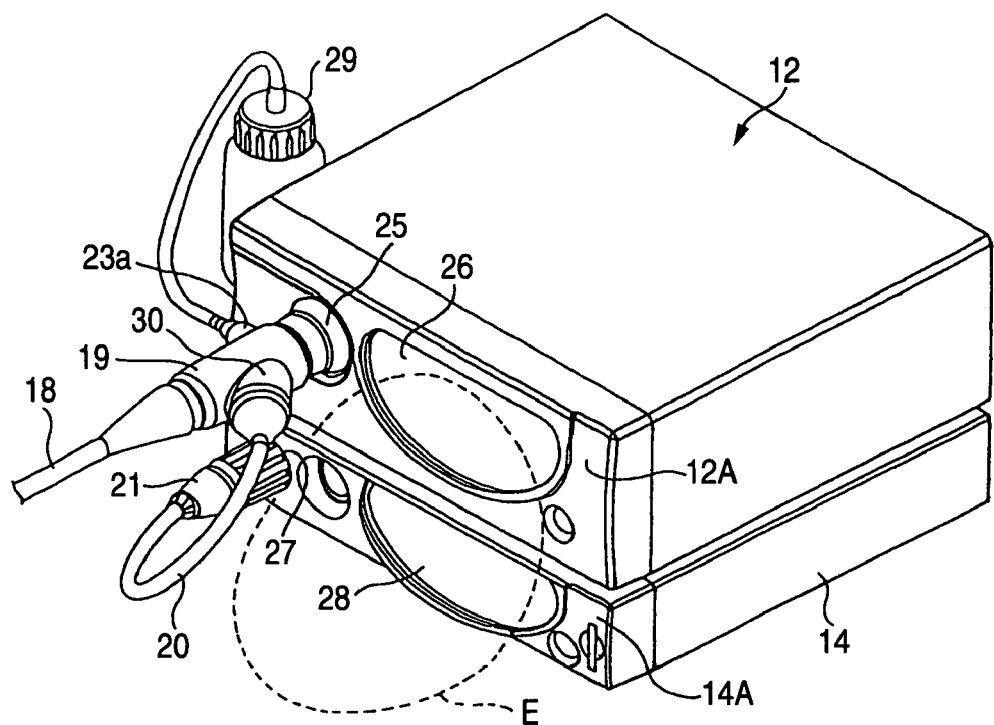
FIG. 1 is a perspective view showing the construction of an endoscope apparatus to which the endoscope connector device according to the embodiments 1-1 and 2-4 of the invention is applied.
Figure 2A:
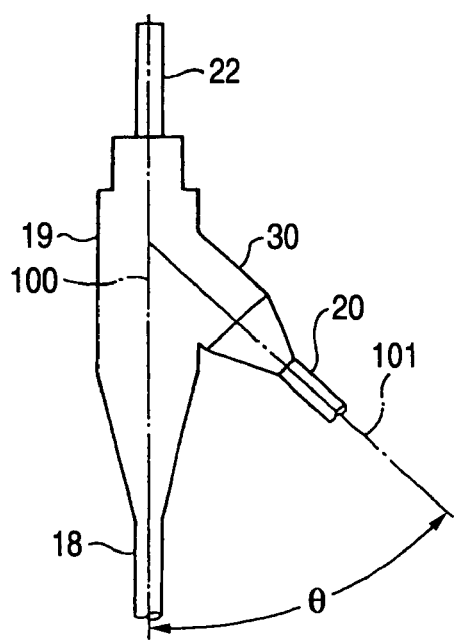
FIG. 2A is a top view showing the relationship between the first cable and the second cable in the light guide connector according to the embodiments 1-1 and 2-4.
Figure 2B:
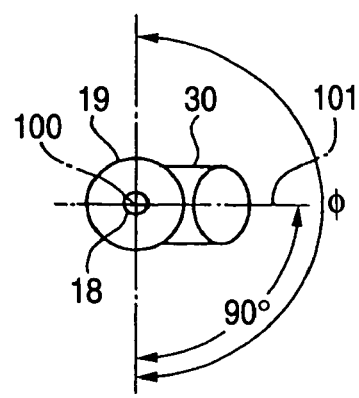
FIG. 2B is a view from the first cable side, showing the relationship between the first cable and the second cable in the light guide connector according to the embodiments 1-1 and 2-4.
Figure 3:
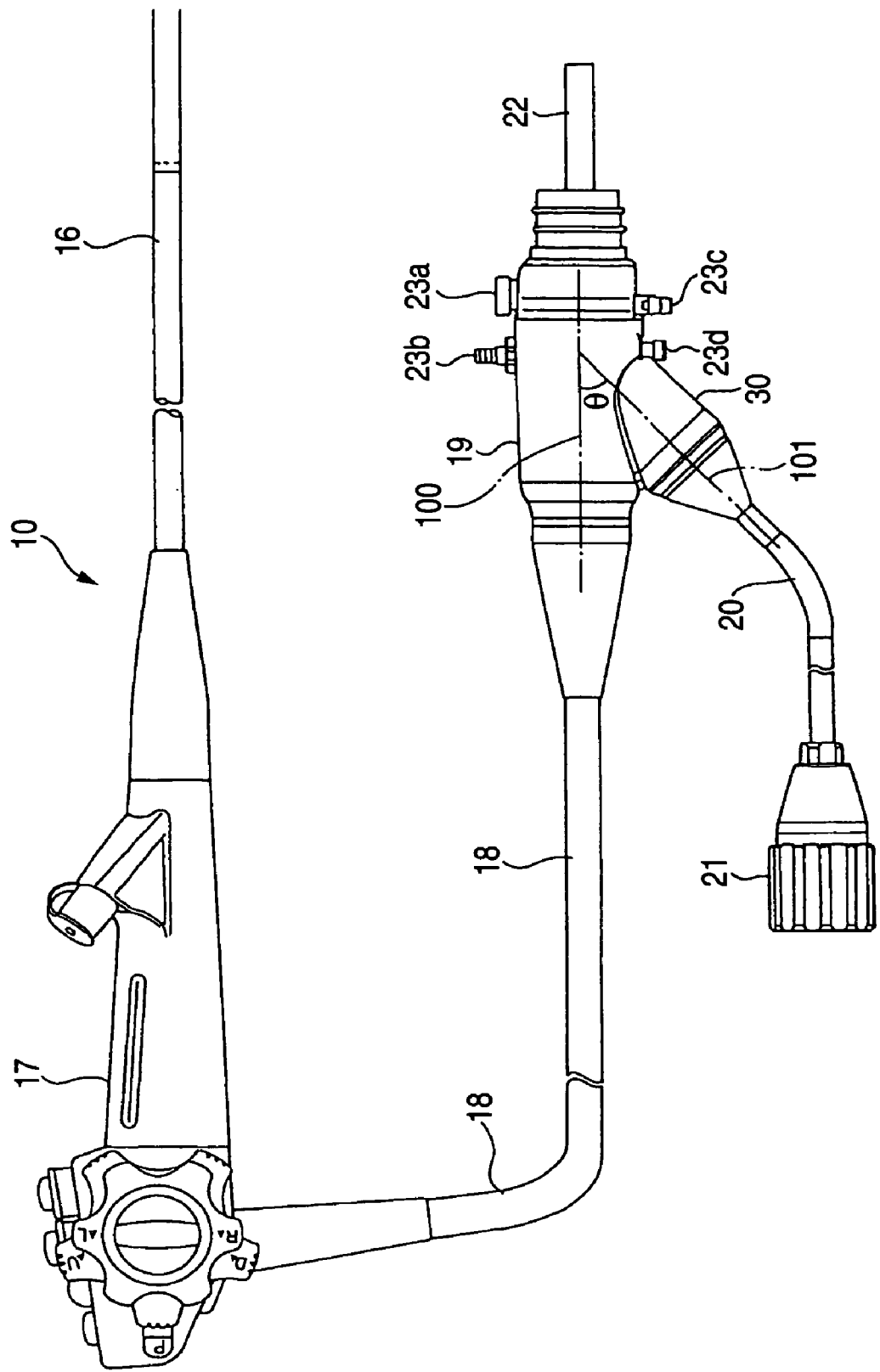
FIG. 3 is a view showing the entire construction of the endoscope of the embodiments 1-1 and 2-4.

FIG. 1 through FIGS. 5A and 5B show the construction of an endoscope connector device according to an embodiment 1-1, wherein FIG. 1 is a perspective view showing a state in that the connector device is connected to a light source unit and a processor unit, and FIG. 3 is an entire construction view of an endoscope (electronic endoscope). The endoscope apparatus includes an endoscope 10 shown in FIG. 3, a light source unit 12 and a processor unit 14 shown in FIG. 1, and a monitor, etc.

In FIG. 3, the endoscope 10 includes a flexible portion 16 that is an insertion portion for a body cavity or the like and has an image pickup device on its distal end, a control portion 17 having an angle operation knob or other various switches, a light guide for guiding illumination light, a first cable 18 that includes: an electric wire for transmitting control signals and video signals; an air/water duct; and the like, the first cable 18 being for connecting these to an external unit, and the like. On the end of this first cable 18, a light guide connector (inserting part) 19 for connection to the light source unit 12, and a second cable 20 and an electric connector (inserting part) 21 for connection to the processor unit 14 are provided.

Namely, on the light guide connector 19, an incidence end 22 of the light guide is formed so as to project, and this connects the light guide laid from the distal end of the flexible portion 16 to the incidence end 22 through the first cable 18 to the light source unit 12. The electric connector 21 connects the electric wire (signal line) laid from the image pickup device installed at the distal end of the flexible portion 16 through the first cable 18 and the second cable 20 to the processor unit 14. In the light guide connector 19, a water supply connector 23a, an air supply connector 23b, a suction connector 23c, and an S terminal 23d are provided.

In FIG. 1, on the front panel 12A of the light source unit 12, a connector receiver 25 to which the light guide connector 19 is connected is provided, and on the right side of this connector receiver 25, an operation panel (touch panel or a push button layout panel) 26, etc., are arranged. On the front panel 14A of the processor unit 14, a connector receiver 27 to which the electric connector 21 is connected is provided, and on the right side of this connector receiver 27, an operation panel (similar to said panel) 28, etc., are arranged. The member 29 on the left side of the units is a water supply tank.

In the light guide connector 19 in such an endoscope 10, in the embodiment 1-1, by providing a lead-out part (having a lead-out ring inside) 30, the second cable 20 is led out diagonally rearward from the right side of the light guide connector and attached. Namely, as shown in FIG. 2A and FIG. 3, in the light guide connector 19, the angle θ between the first cable axial direction 100 as the center axis direction of the first cable 18 and the second cable axial direction 101 as the center axis direction of the second cable 20 (angle within a horizontal plane measured from the first cable 18 side when viewing the light guide connector 19 from above) is set to, for example, 45 degrees. This angle θ is set within the range of $0°<θ<90°$ or $0°≦θ≦80°$, or more preferably, $30°≦θ≦60°$.

Figure 4A:
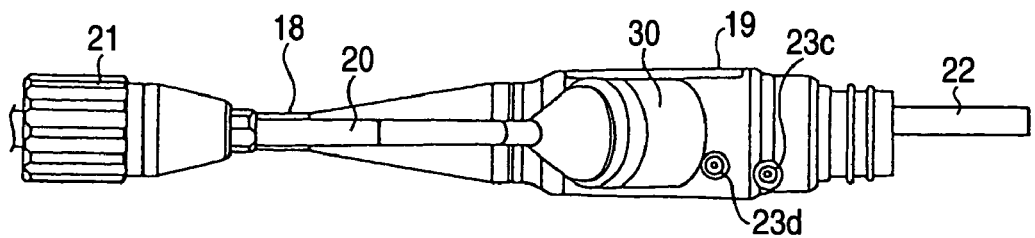
FIG. 4A is a view of the surrounding of the light guide connector being connected from the right side surface, the view corresponding to FIG. 3 when the second cable is arranged horizontally.

As shown in FIG. 2B and FIG. 4A, the leading-out direction of this second cable 20 is maintained at a horizontal position by the lead-out part 30 (when the light guide connector is connected). FIG. 2B is a view of FIG. 2A from the first cable 18 side, wherein the second cable axial direction 101 is maintained horizontally by attaching the lead-out part 30 horizontally on the right side of the light guide connector 19. Basically, this second cable 20 is led out from the right side of the light guide connector 19, and in the embodiment 1-1, as shown in FIG. 2B, when the angle measured from the lower side of the vertical line of the first cable axial direction 101 is defined as φ, this angle is set within the range of $0°<φ<180°$. The light guide connector 19 is cylindrical, however, the connecting position in its rotation direction is fixed according to the set position of the light guide incidence end 22.

Figure 4B:
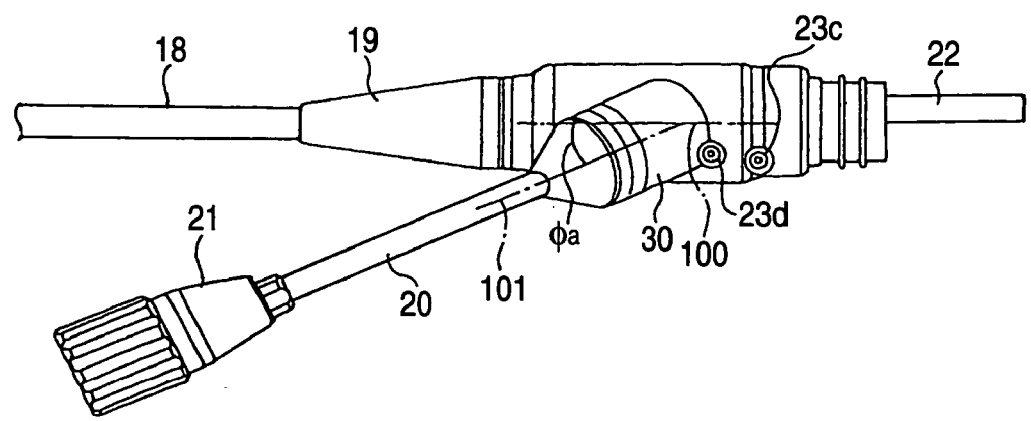
FIG. 4B is a view of the surrounding of the light guide connector being connected from the right side surface, when the second cable is inclined downward from the horizontal position.
Figure 5A:
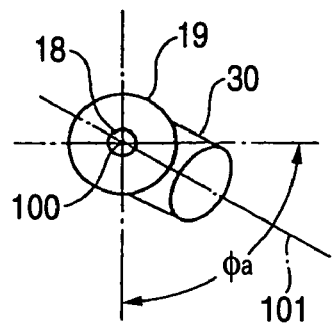
FIG. 5A is a view when the second cable is inclined downward from the horizontal position according to the processor unit placed below.

As the angle (φ) in the vertical direction, the following values can be selected according to the layout condition of the light source unit 12 and the processor unit 14. In FIG. 4B, as shown in FIG. 1, an example in the case where the processor unit 14 is placed below the light source unit 12 is shown, and when the light guide connector is connected, the second cable 20 can be attached by being turned down by an angle $φ_a$ of, for example, 30 degrees (the angle between the first cable axial direction 100 and the second cable axial direction 101 viewed from the side) from its horizontal position. Namely, as shown in FIG. 5A, this angle is set within the range of $0°<φ_a<90°$ from the horizontal position to the downward side.

Figure 5B:
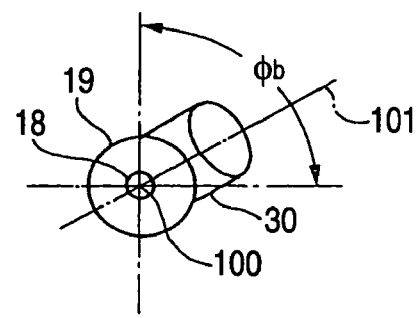
FIG. 5B is a view when the second cable is inclined upward from the horizontal position according to the processor unit placed above.

On the other hand, contrary to FIG. 1, when the processor unit 14 is stacked on the light source unit 12, as shown in FIG. 5B, when the light guide connector is connected, the second cable 20 can be attached by being turned upward by an angle $φ_b$ (angle between the first cable axial direction 100 and the second cable axial direction 101 viewed from the side) of approximately 30 degrees from its horizontal position. This angle $φ_b$ is set within a range of $0°<φ_b<90°$ from the horizontal position to the upward side. Thus, by inclining the second cable 20 to the processor unit 14, the second cable 20 is arranged in a natural state, and the load to be burdened by this second cable 20 on the base end of the light guide connector 19 or the lead-out part 30 can be reduced.

The embodiment 1-1 is constructed as described above, wherein when the light guide connector 19 and the electric connector 21 are connected to the light source unit 12 and the processor unit 14, the state shown in FIG. 1 is obtained. As seen in this FIG. 1, the second cable 20 is led diagonally rearward from the side surface of the light guide connector 19 by the lead-out part 30, so that in front of the front panels 12A and 14A of the light source unit 12 and the processor unit 14, a wide space shown as E is created. Therefore, the operation to access to the operation panels 26 and 28, etc., provided on the front panels 12A and 14A becomes easy. In addition, since the second cable 20 is arranged on the right side of the light guide connector 19, it is possible that the light guide connector 19 and the electric connector 21 are easily connected by the right hand while the endoscope control portion 17 is held by the left hand. In addition, the distance between the first cable 18 and the second cable 20 does not become short, so that high cleaning performance is maintained, and the curvature when the second cable 20 is attached and connected does not become small.

Figure 6A:
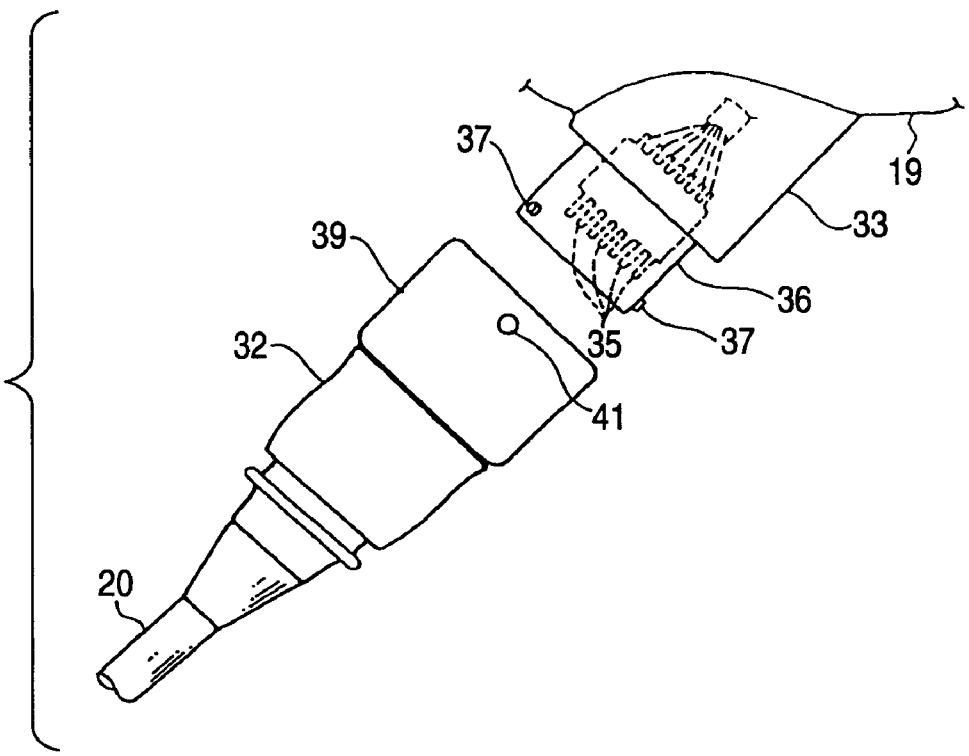
FIG. 6A is a view showing a construction relating to the intermediate connector of the embodiment 1-2, before the connector is connected.
Figure 6B:
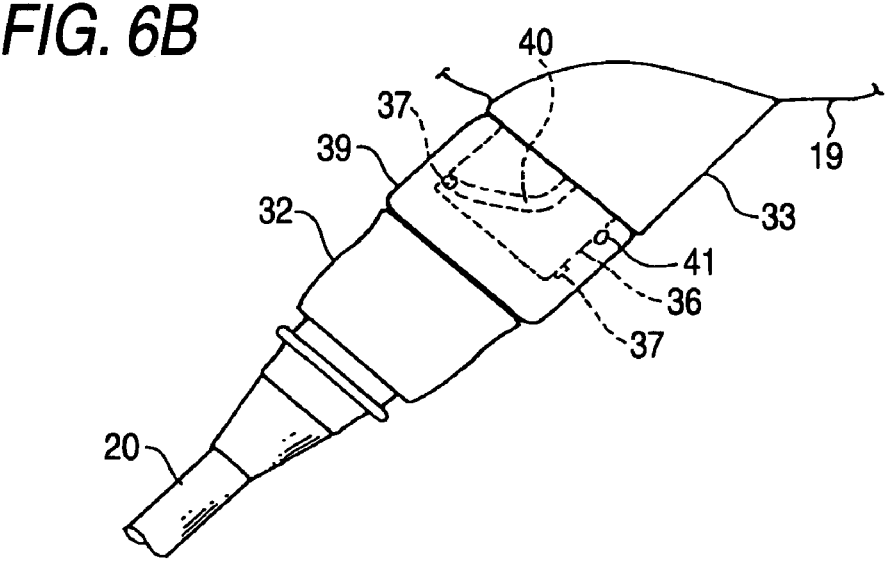
FIG. 6B is a view showing a construction relating to the intermediate connector of the embodiment 1-2, after the connector is connected.
Figure 7:
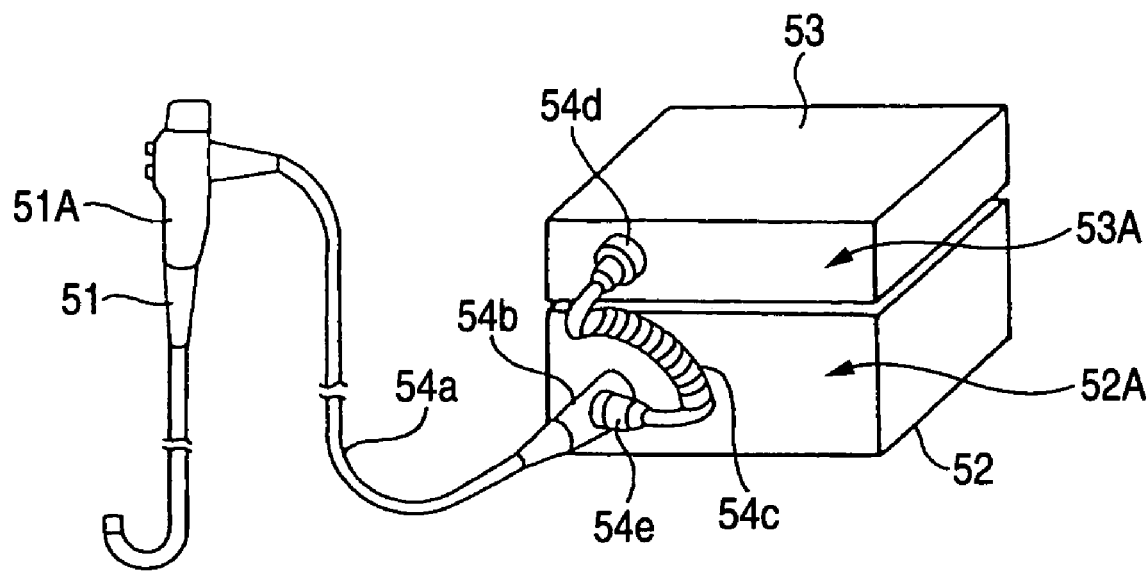
FIG. 7 is a perspective view showing an example of the related-art connector connection of an endoscope apparatus.

In FIG. 6A and FIG. 6B, the construction of an endoscope connector device according to an embodiment 1-2 is shown, and in this embodiment 1-2, the second cable 20 is made attachable and detachable by an intermediate connector 32 in the light guide connector 19. As shown in FIGS. 6A and 6B, the intermediate connector (inserting part) 32 provided on the second cable 20 side is constructed so as to be connected to the lead-out part (connector receiving part) of the light guide connector 19 side, and inside this lead-out part 33, for example, a male pin 35 for the electric connector provided inside and engaging pins 37 are provided on three points of the outer circumference of the receiving ring 36. On the other hand, the intermediate connector (inserting part) 32 is provided with female pins inside and a fixing ring 39 that rotates in a predetermined range is provided on the outer circumference. Inside this fixing ring 39, guide grooves 40 that engage with the engaging pins 37 are formed on three points, and on the outer circumference, a mark 41 indicating the upper position is provided.

According to this embodiment 1-2, as shown in FIG. 6A, the intermediate connector 32 is inserted into the lead-out part 33 by turning the mark 41 to the upside, and the fixing ring 39 is rotated clockwise and fastened, as shown in FIG. 6B, the engaging pins 37 are guided to the insides of the guide grooves (grooves in the inserting direction, grooves inclined diagonally, and grooves in the rotating direction), whereby the intermediate connector 32 is tightly fixed to the lead-out part 33 (it is fixed when the engaging pins 37 are positioned in the grooves in the rotating direction).

According to this embodiment 1-2, the second cable 20 becomes disconnectable from the first cable 18 by the intermediate connector 32, so that handling when cleaning or connecting the connector becomes easy. In addition, even in this embodiment 1-2, the intermediate connector 32 is also arranged on the right side of the light guide connector 19 so that the second cable 20 is led out from the right side of the light guide connector 19, so that the intermediate connector 32 can be easily connected to the light guide connector 19 by the right hand.

Second Embodiment

Figure 9:
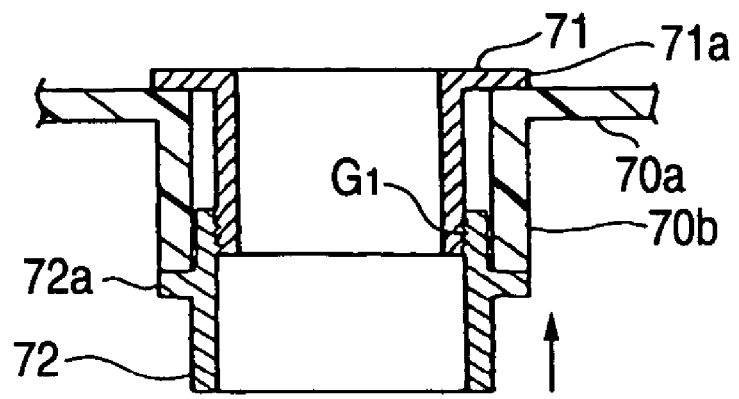
FIG. 9 is a sectional view showing the construction of the endoscope cable lead-out unit according to the embodiment 2-1 of the invention.
Figure 10:
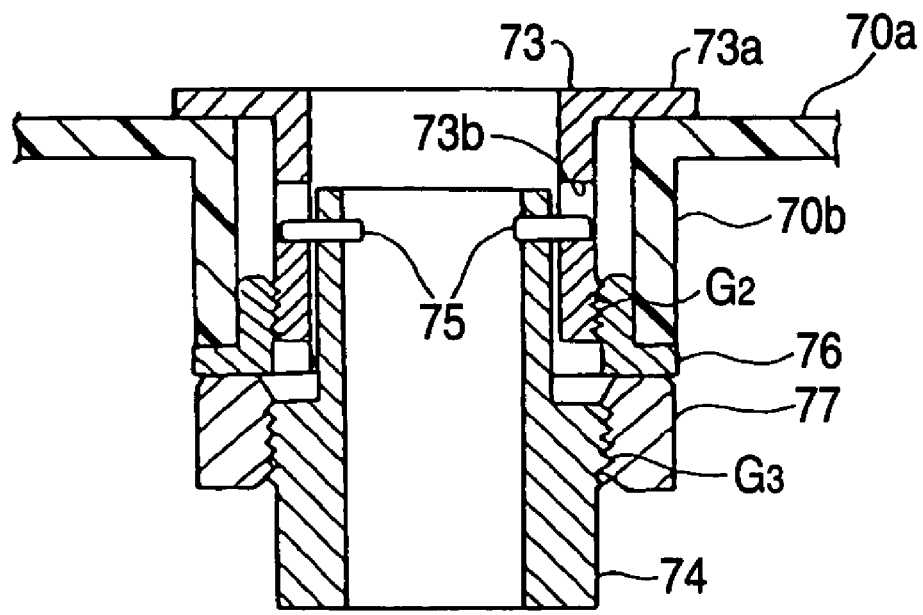
FIG. 10 is a sectional view showing the construction of the endoscope cable lead-out unit according to the embodiment 2-2.
Figure 11:
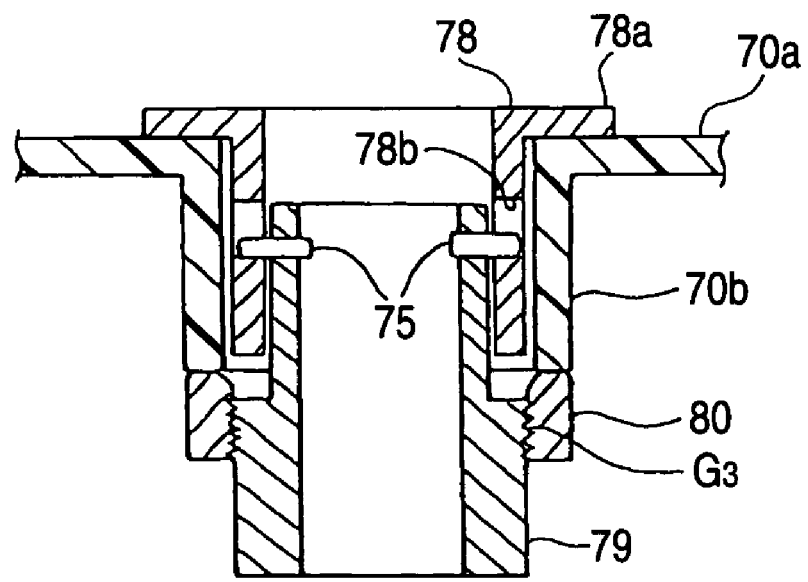
FIG. 11 is a sectional view showing the construction of the endoscope cable lead-out unit according to the embodiment 2-3.

FIG. 9 through FIG. 11 show a basic construction of an endoscope cable lead-out unit of the invention, wherein FIG. 9 shows an embodiment 2-1, FIG. 10 shows an embodiment 2-2, and FIG. 11 shows an embodiment 2-3. In FIG. 9, a cylindrical lead-out part outer sheath 70b is integrally formed from a synthetic resin material (hard) in the leading-out direction from an outer sheath of the main body of the light guide connector, etc., and inside the outer sheath 70b, a cylindrical frame 71 that is made of metal is arranged, and the outer circumferential edge 71a of this frame 71 is constructed so as to engage and come into contact with the base end side (cylinder bottom surface) of the outer sheath 70b. This frame 71 is provided with a presser ring 71 so as to be screwed and coupled to a screwing portion $G_1$ at the distal end side, and the outer circumferential projection (flange portion) 72a of this presser ring 72 is engaged to be contacted with the distal end face of the outer sheath 70b.

According to this embodiment 2-1, the presser ring 72 is coupled to and screwed into the frame 71 disposed inside the outer sheath 70b via the screwing portion $G_1$, whereby the outer sheath 70b is nipped vertically by the projection 72a of the presser ring 72 and the outer circumferential edge 71a of the frame 71, whereby the frame 71 can be securely fixed to the inner side of the synthetic resin-including outer sheath 70b. The cable including the electric wire or the like is fixed to the frame 71 or the like.

In the case of the embodiment 2-2 of FIG. 10, on the base end side (main body side), a cylindrical first frame 73 having an outer circumferential edge 73a and a cylindrical second frame 74 that fits the inner circumferential surface of the frame 73 are provided, and this first frame 73 is provided with a guide groove 73b that extends from the distal end side (the lower side of the figure) to the latching position, and the second frame 74 is attached with pins 75 that are latched by being guided by this guide groove 73b. On the distal end side outer circumference of the first frame 73, a temporary (second) presser ring 76 is provided that is coupled to a screwing portion $G_2$ and comes into contact with and presses the distal end face of the outer sheath 70b, and on the middle outer circumference of the second frame 74, a temporary presser ring 77 that is coupled to a screwing portion $G_3$ is provided, and this presser ring 77 is constructed so as to press the lead-out part outer sheath 70b via (by contact with the lower surface thereof) the temporary presser ring 76.

According to this embodiment 2-2, first, the first frame 73 is disposed inside the outer sheath 70b and then the temporary presser ring 76 is coupled to the screwing portion $G_2$ there, whereby the temporary presser ring 76 and the outer circumferential edge 73a of the first frame 73 nip the outer sheath 70b. Thereafter, while fitting the second frame 74 to the first frame 73, the pins 75 are inserted through the guide grooves 73b to latch the second frame 74 at a predetermined position, and the presser ring 77 coupled to the screwing portion $G_3$ is rotated and fastened, whereby (the end face of) the presser ring 77 and the outer circumferential edge 73a of the first frame 73 nip the outer sheath 70b via the temporary presser ring 76, whereby the first frame 73 and the second frame 74 can be securely fixed to the inner surface of the synthetic resin-including outer sheath 70b.

The embodiment 2-3 of FIG. 11 shows an example in the case where no temporary presser ring is used in the construction of the embodiment 2-2, and as in the case of the embodiment 2-2, the second frame 79 is attached to the first frame 78 via the guide groove 78b and the pins 75. The presser ring 80 that is coupled to the screwing portion $G_3$ on the middle outer circumference of the second frame 79 is disposed so as to come into direct contact with the distal end face of the outer sheath 70b. In the case of this embodiment 2-3 also, by fastening the presser ring 80, the outer sheath 70b can be nipped by the presser ring 80 and the outer circumferential edge 78a of the first frame 78 and both frames 78 and 79 can be securely fixed to the inner surface side of the outer sheath 70b.

As described above, in the embodiments 2-1 to 2-3, the frame 71, the first frames 73 and 78, and the second frames 74 and 79 are arranged on the inner surface side of the outer sheath 70b, and a cable (or components thereof) is retained by these frames, so that the outer sheath 70b is prevented from being broken due to stress concentration.

In the embodiments 2-2 and 2-3, the second frames 74 and 79 that retain a cable including an electric wire and the like are detachably attached to the first frames 73 and 78, so that assembling of the cable to the lead-out part becomes easy.

FIG. 1 through FIG. 3 and FIG. 12 through FIGS. 14A and 14B show an endoscope cable lead-out unit of an embodiment 2-4 and a construction of an endoscope to which this endoscope cable lead-out unit is applied, and this embodiment 2-4 uses the basic construction of the embodiment 2-2 (and the second cable fixing type). FIG. 1 is a perspective view showing a state in that a light guide connector and an electric connector are connected to a light source unit and a processor unit, and FIG. 3 is an entire construction view of an endoscope, and an endoscope apparatus includes the endoscope 10 shown in FIG. 3, the light source unit 12 and the processor unit 14 shown in FIG. 1, and a monitor, etc.

In FIG. 3, the endoscope 10 has a flexible portion that is an insertion portion for a body cavity or the like and has an image pickup device on its distal end, a control portion 17 having an angle operation knob and other various switches, and a first cable 18 that includes: a light guide for guiding illumination light; an electric wire for transmitting control signals and video signals; and air/water duct, the first cable being for connecting these to an external unit. On the end of this first cable 18, a light guide connector (inserting part) 19 for linking to the light source unit 12 and a second cable 20 and an electric connector (inserting part) 21 for linking to the processor unit 14 are provided.

Namely, the light guide connector 19 has an incidence end 22 for a light guide formed so as to project, whereby a light guide installed through the first cable 18 from the distal end of the flexible portion 16 is connected to the light source unit 12. In addition, the electric connector 21 connects the electric wire (signal line) installed through the first cable 18 and the second cable 20 from the image pickup device provided on the distal end of the flexible portion 16 to the processor unit 14. The light guide connector 19 is provided with a water supply connector 23a, an air supply connector 23b, a suction connector 23c, and an S terminal 23d.

In FIG. 1, on the front panel 12A of the light source unit 12, a connector receiver 25 to which the light guide connector 19 is connected is provided, and on the right side of this connector receiver 25, an operation panel 26 and the like are arranged. On the front panel 14A of the processor unit 14, a connector receiver 27 to which the electric connector 21 is connected is provided, and on the right side of this connector receiver 27, an operation panel 28 and the like are arranged. The member 29 on the left side of the units is a water supply tank.

In the light guide connector 19 of the endoscope 10 thus constructed, according to the fourth embodiment, the second cable 20 is led out diagonally rearward from the right side of the light guide connector 19 and attached by providing a lead-out part 30. Namely, as shown in FIG. 2A and FIG. 3, in the light guide connector 19, the angle θ between the first cable axial direction 100 as the central axial direction of the first cable 18 and the second cable axial direction 101 as the central axis direction of the second cable 20 (the angle within a horizontal plane measured from the first cable 18 side when viewing the light guide connector 19 from above) is set to, for example, 45 degrees. This angle θ is set within the range of $0° < θ < 90°$.

FIG. 2B is a view of FIG. 2A from the first cable 18 side, wherein the lead-out part 30 is attached horizontally on the right side of the light guide connector 19, and the second cable axial direction 101 is maintained horizontally (when the light guide connector is connected).

Figure 12:
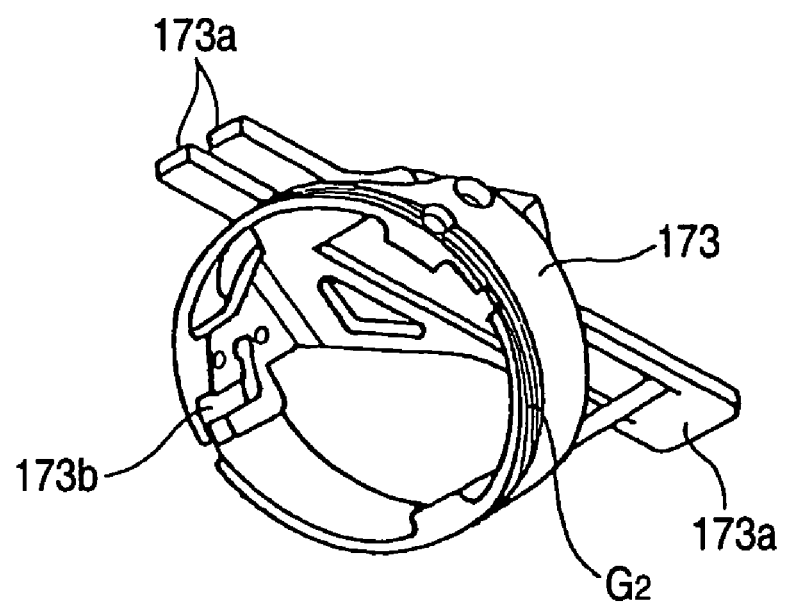
FIG. 12 is a perspective view showing the construction of the first frame used in the embodiments 2-4 and 2-5.

FIG. 12 shows the construction of the first frame 173 to be used in the embodiment 2-4 (and the embodiment 2-5), and on the bottom surface side (the upper side of the figure) of this first frame 173, plate-shaped edge parts (frame edge parts) 173a for engaging with two points of the base end side of the synthetic resin-including outer sheath 170b (FIGS. 13A and 13B) of the lead-out part 30 is provided. On the cylindrical main body inner circumferential surface of the first frame 173, a guide groove 173b is formed and a screw part for the screwing portion G2 is formed on the distal end side of the outer circumferential surface.

Figure 13A:
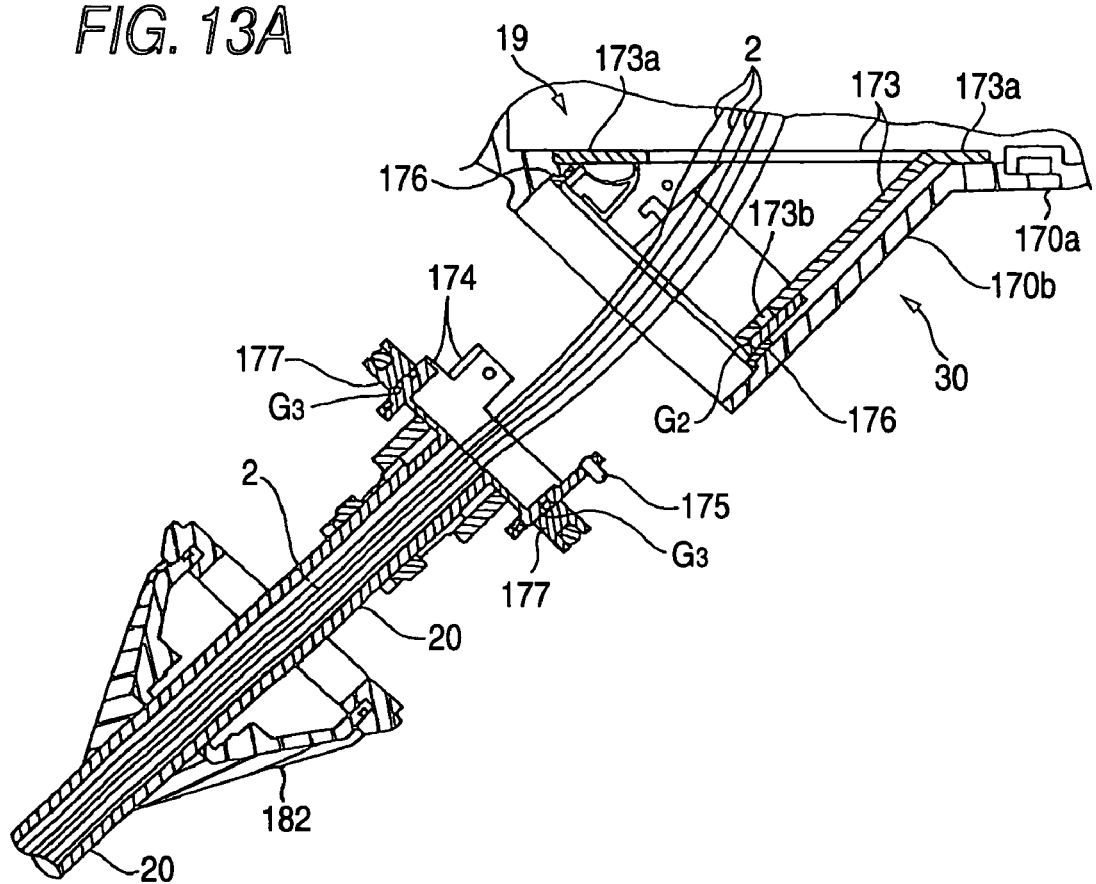
FIGS. 13A and 13B are sectional views showing the states before assembling the cable lead-out unit according to the embodiment 2-4 in order.
Figure 13B:
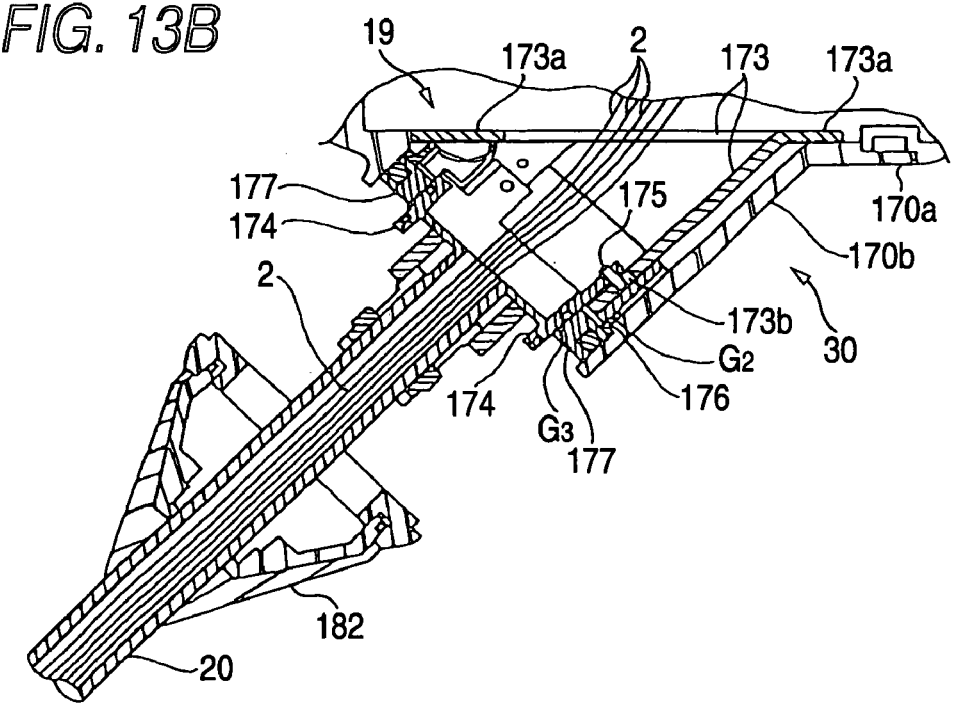
Figure 14A:
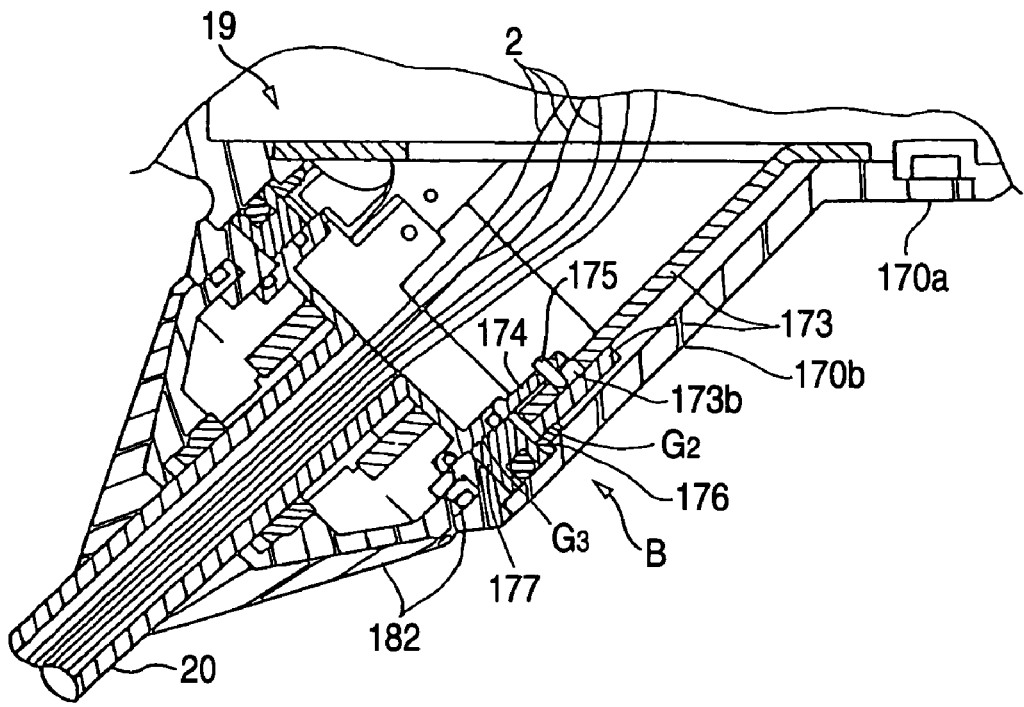
FIG. 14A is a view showing the construction of the cable lead-out unit according to the embodiment 2-4, after assembling.
Figure 14B:
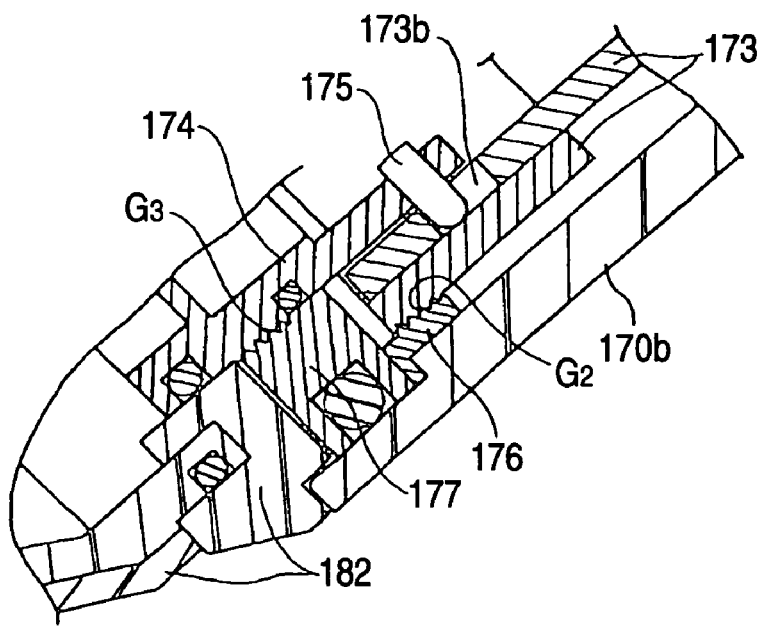
FIG. 14B is an enlarged view of the portion shown by the arrow B of FIG. 14A.

As shown in FIGS. 13A and 13B and FIGS. 14A and 14B (FIG. 14B is an enlarged view of the portion indicated by the arrow B of FIG. 14A), the first frame 173 is disposed inside the outer sheath 170b of the lead-out part 30, and as in the case of FIG. 10, it is temporarily fixed to the outer sheath 170b by coupling the temporary presser ring 176 to the screwing portion $G_2$. In addition, a second frame 174 is provided which has an outer circumferential surface fit to the inner circumferential surface of this first frame 173, and to this second frame 174, a pin 175 that is guided by the guide groove 173b and latches is attached, and a presser ring 177 is screwed and arranged on the screwing portion $G_3$ on the outer circumference. To this second frame 174, a cable 20 including an electric wire 2 is attached, and on the cable side of this second frame 174, a synthetic resin-including cover 182 that protects the cable 20 is provided.

The embodiment 2-4 is constructed as described above, and in FIG. 13A, first, the first frame 173 is temporarily fixed to the outer sheath 170b by the temporary presser ring 176. From this state of FIG. 13A, the second frame 174 is fit to the first frame 173 and the pin 175 is latched through the guide groove 173b to fasten the presser ring 177, whereby the outer sheath 170b can be nipped by the presser ring 177 and the edge 173a of the first frame 173 (via the temporary presser ring 176) as shown in FIG. 13B. Thereby, the frames 173 and 174 and the second cable 20 are securely fixed to the outer sheath 170b. Last, by attaching a cover 182, the state of FIGS. 14A and 14B is obtained.

In addition, in this embodiment 2-4, as shown in FIG. 1, the second cable 20 is led diagonally rearward from the side surface of the light guide connector 19 by the lead-out part 30, so that in front of the front panels 12A and 14A of the light source unit 12 and the processor unit 14, a wide space indicated by E is created. Therefore, the operation to access the operation panels 26 and 28, etc., arranged on the front panels 12A and 14A becomes easy. In addition, since the second cable 20 is arranged on the right side of the light guide connector 19, the light guide connector 19 and the electric connector 21 can be easily connected by the right hand while the endoscope control portion 17 is grasped by the left hand.

Figure 15:
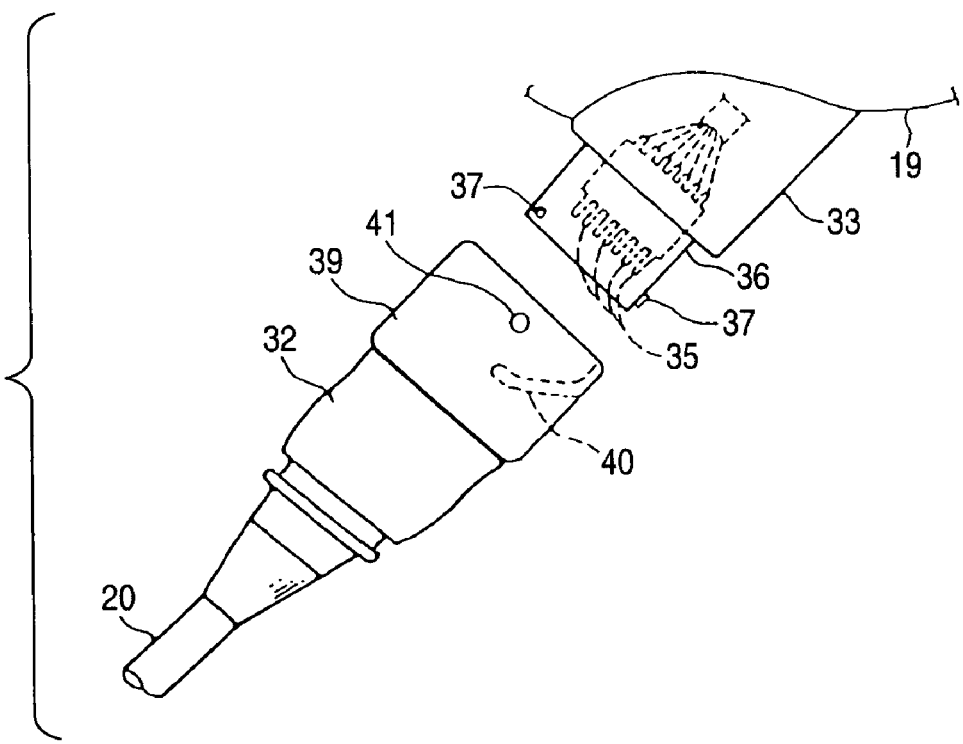
FIG. 15 shows the exterior construction of the endoscope cable lead-out unit according to the embodiment 2-5.

FIG. 15 through FIGS. 17A and 17B show the construction of an endoscope cable lead-out unit according to an embodiment 2-5, and this construction of the embodiment 2-5 is similar to that of the embodiment 2-4 (uses the basic construction of the embodiment 2-2) except that an intermediate connector 32 is disposed on the lead-out part 33 of the light guide connector 19 to make the second cable 20 detachable. As shown in FIG. 15, the intermediate connector (inserting part) 32 provided on the second cable 20 side is constructed so as to be connected to the lead-out part (connector receiver) 33 of the light guide connector 19 side, and this lead-out part 33 is provided with, for example, male pins 35 for an electric connector inside, and on, for example, three points of the outer circumference of the receiver ring 36, engaging pins 37 are provided. On the other hand, the intermediate connector (inserting part) 32 is provided with female pins inside and, on the outer circumference, a fixing ring 39 that rotates in a predetermined range. On this fixing ring 39, guide grooves 40 that engage with the engaging pins 37 are formed inside at three points, and on the outer circumference, a mark 41 indicating the upper position is provided.

Figure 16:
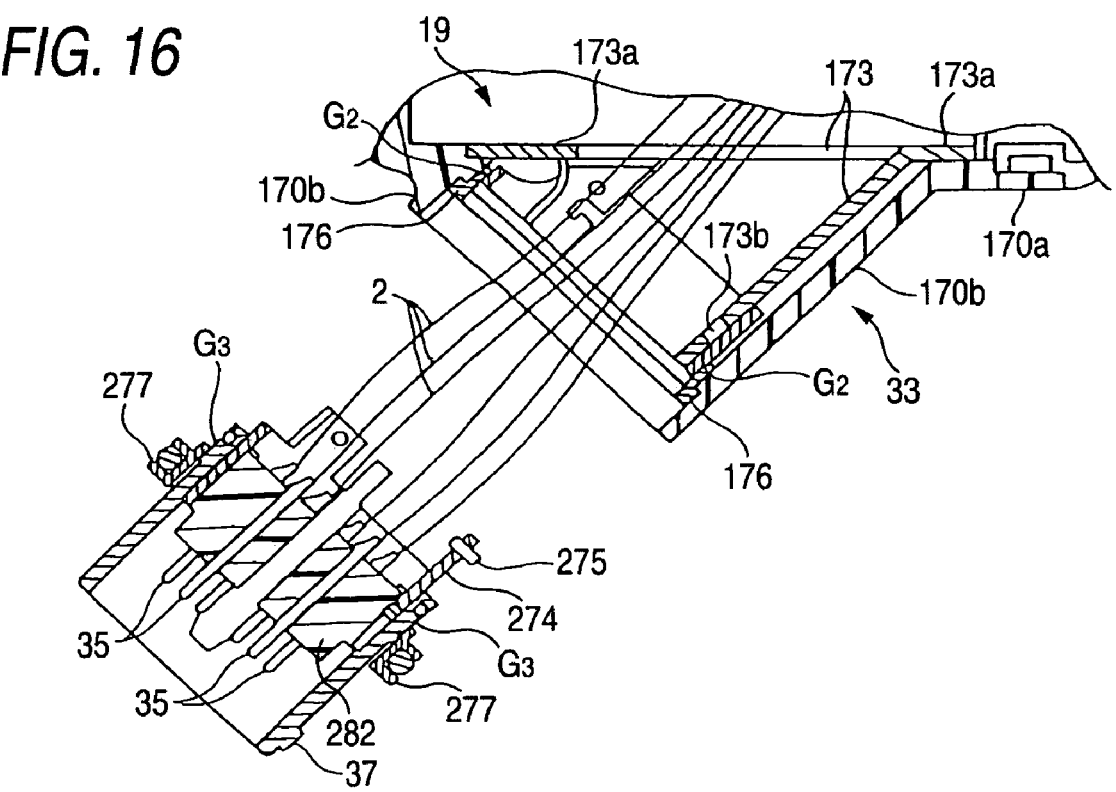
FIG. 16 is a sectional view of the state before assembling the cable lead-out unit according to the embodiment 2-5 in order.

In this embodiment 2-5, the first frame 173 of FIG. 12 is also provided, and as shown in FIG. 16, this first frame 173 is provided inside the outer sheath 170b of the lead-out part 33, and is temporarily fixed to the outer sheath 170b by coupling the temporary presser ring 176 to the screwing portion $G_2$ as in the case of FIG. 10. In addition, on the inner circumferential surface of this first frame 173, a second frame 274 having an outer circumferential surface to fit the inner circumferential surface is provided, and to this second frame 274, a pin 275 that is guided by the guide groove 173b of the first frame 173 and latched is attached, and to a screwing portion $G_3$ on the outer circumference thereof, a presser ring 277 is set and screwed. Inside this second frame, a pin supporting member 282 provided with connector pins 35 is attached.

Figure 17A:
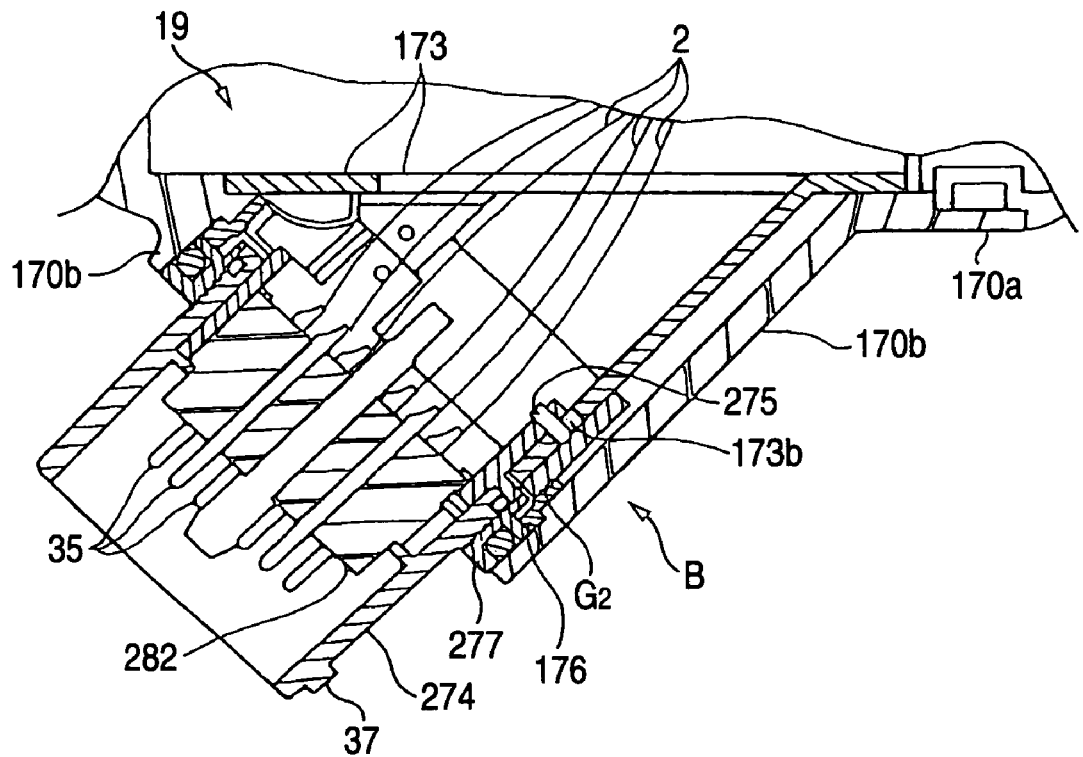
FIG. 17A is a view showing the construction of the cable lead-out unit according to the embodiment 2-5, after assembling.
Figure 17B:
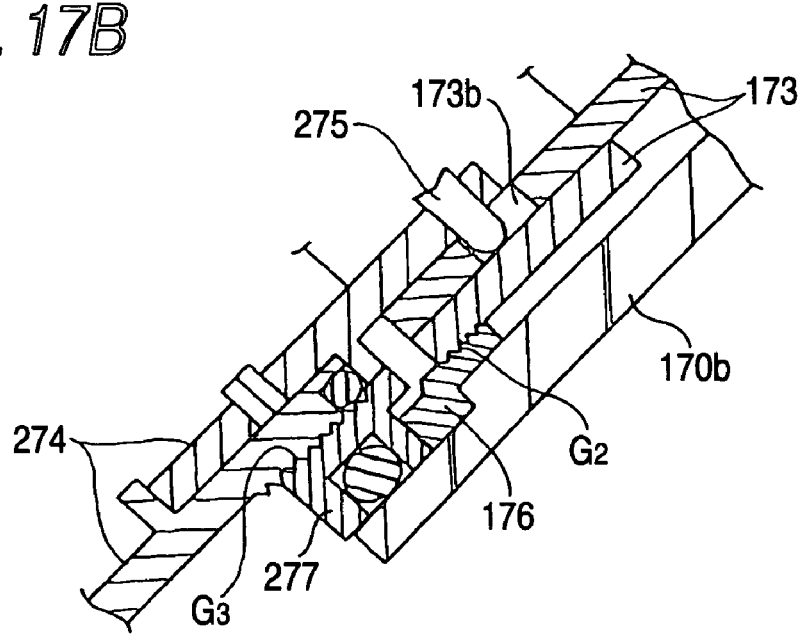
FIG. 17B is an enlarged view of the portion shown by the arrow B of FIG. 17A.
Figure 18A:
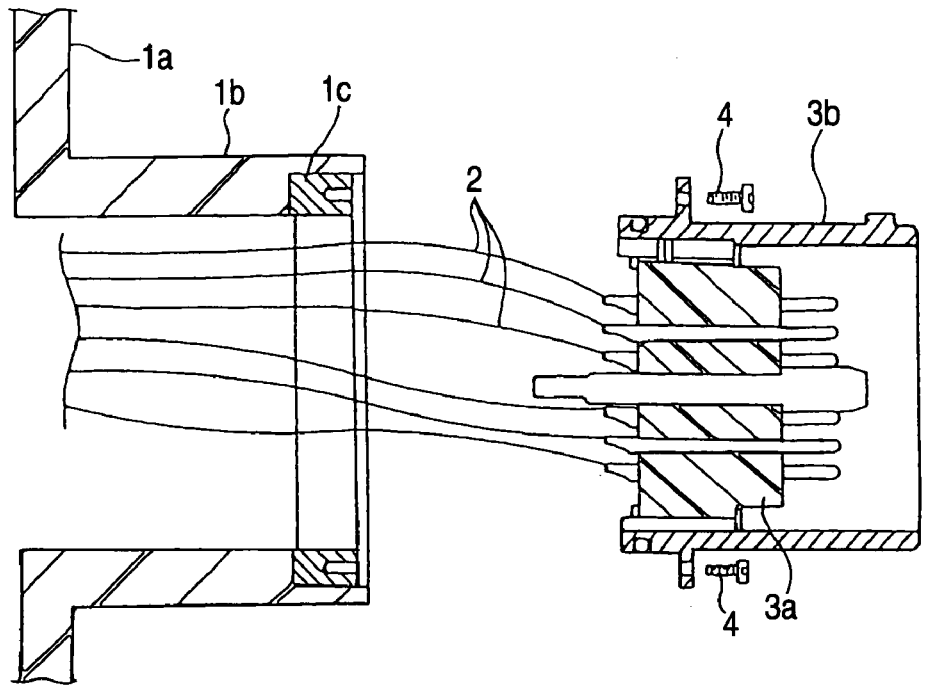
FIGS. 18A and 18B are sectional views showing the construction of the related-art endoscope cable lead-out unit.
Figure 18B:
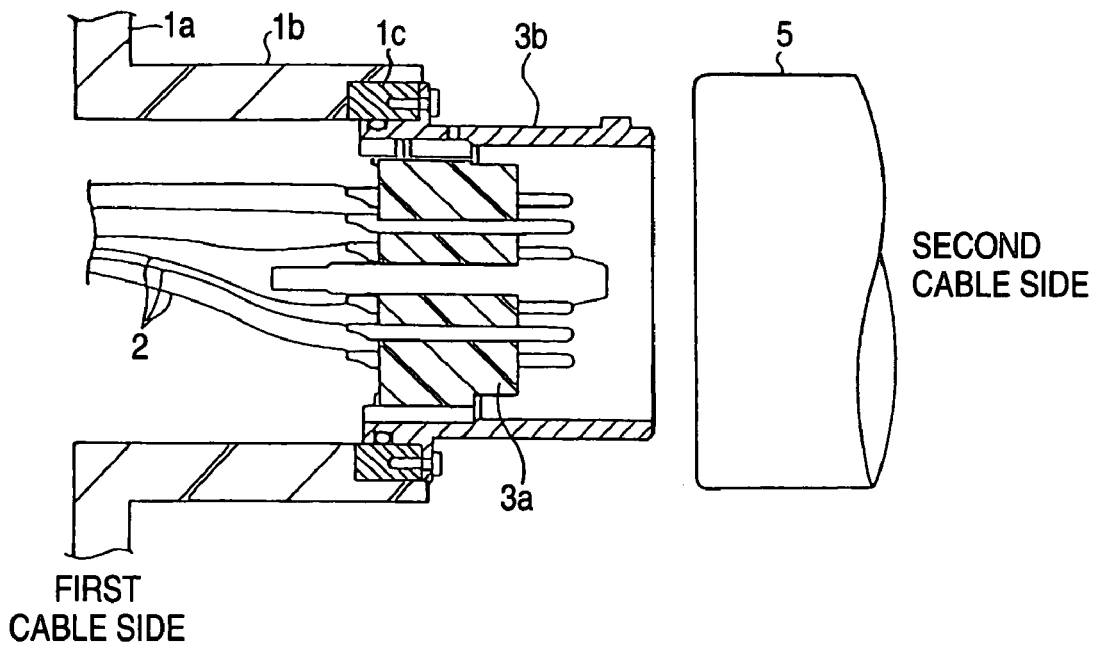

The embodiment 2-5 is constructed as described above, and in FIG. 16, the first frame 173 is temporarily fixed to the outer sheath 170b by the temporary presser ring 176, and from this state of FIG. 16, the second frame 274 is fit to the first frame 173, the pin 275 is latched by the guide groove 173b, and the presser ring 277 is fastened, whereby the outer sheath 170b is nipped by the presser ring 277 and the edge 173a of the first frame 173 vertically as shown in FIG. 17A. Thereby, the frames 173 and 274 and the pin supporting member 282 are securely fixed to the outer sheath 170b.

Then, as shown in FIG. 15, the intermediate connector 32 is inserted into the lead-out part 33, and the fixing ring 39 is rotated clockwise so as to be fastened, whereby the engaging pins 37 are guided to the insides of the guide grooves 40 and the intermediate connector 32 is linked to the lead-out part 33. According to this embodiment 2-5, the second cable 20 is made disconnectable from the first cable 18 by the intermediate connector 32, so that handling in cleaning or connector connection becomes easy. In this embodiment 2-5, the second cable 20 is also led diagonally rearward from the side surface of the light guide connector 19 by the lead-out part 33 as shown in FIG. 1.

In the above-described embodiments, a cable including an electric wire is led out from the main body, however, in an endoscope, in addition to this electric wire, linear members such as a light guide, an air duct, an water duct, a driving force linear transmitting member, and the like are installed, and the invention can be applied for leading-out these linear members from the main bodies of various units.

According to the endoscope connector device of this invention, the operation space in front of the front panel becomes wider, access to the front panel operation part becomes easy, and since the second cable is arranged on the right side, it becomes possible for a user to hold the endoscope control portion by the left hand and easily connect the light guide connector and the electric connector by the right hand, and even when the second cable becomes detachable due to the intermediate connector as in the case according to the second aspect, the intermediate connector of the second cable can be easily connected or disconnected by the right hand.

Figure 8:
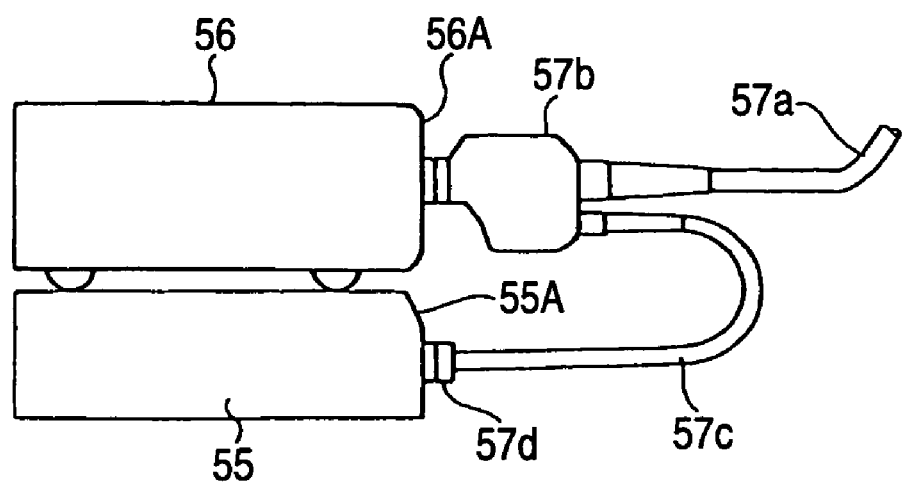
FIG. 8 is a side view showing another example of the related-art connector connection of an endoscope apparatus.

Furthermore, in comparison with the related-art construction of FIG. 8, the distance between the first cable and the second cable does not become narrow, so that high cleaning performance is maintained, and since the curvature of the second cable when it is attached and connected does not become small, a load is not burdened on the second cable. As in the case of Japanese Published Unexamined Patent Application No. H05-228104, it can also be prevented that the light guide connector (inserting part) and the electric connector (inserting part) swing and break each other.

With the construction according to the third aspect, even when the light source unit is above or below the processor unit, the second cable faces the processor unit from the light guide connector, so that natural connection and layout are obtained, and the load to be burdened by the second cable on the base end (root) of the light guide connector is reduced.

According to the endoscope cable lead-out unit of the invention, since a cable or components of the cable are retained by the metallic frame, a stress generated due to load of the cable does not concentrate at the synthetic resin-including outer sheath, and the outer sheath is prevented from being broken. Furthermore, leading-out and assembling of the cable become easy.

With the construction according to the fifth aspect, since the cable is retained by the second frame that is detachably attached to the first frame of the lead-out part, the cable can be easily laid at the lead-out part while being securely fixed to the second frame, whereby arrangement and assembling of the cable with respect to the lead-out part become easy.

With the construction according to the sixth aspect, even when the second cable including an electric wire is led out diagonally rearward from the light guide connector to which the first cable including a light guide and the electric wire is connected, the lead-out part that may not be broken can be easily assembled without using a complicated construction.

The entire disclosure of each and every foreign patent application from which the benefit of foreign priority has been claimed in the present application is incorporated herein by reference, as if fully set forth.

What is claimed is:

1. An endoscope device comprising:
    an endoscope connector device comprising
        a first cable of an endoscope, including a light guide for supplying illumination light and an electric wire for obtaining video signals from an image pickup device;
        a light guide connector connected to the first cable; and
        a second cable of the endoscope, including the electric wire led out of the light guide connector,
        wherein the second cable is attached diagonally from the light guide connector at an angle $\theta$ within a range of $30° \leq \theta \leq 60°$ from a first cable side of an axial direction of the first cable;
    a light source unit that connects to the first cable via the light guide connector; and
    a video signal processor unit that connects to the second cable via an electric connector;
    wherein the second cable is arranged on a right side of the light guide connector, the light guide connector being connected to the light source unit so as to face a front panel of the light source unit,
    wherein, when the processor unit is arranged below the light source unit, the second cable is attached so as to turn downward at an angle $\phi_a$ in a range of $0° < \phi_a < 90°$ from its horizontal position at which the light guide connector is connected, and
    wherein, when the processor unit is arranged above the light source unit, the second cable is attached so as to turn upward at an angle $\phi_b$ in a range of $0° < \phi_b < 90°$ from its horizontal position at which the light guide connector is connected.

2. The endoscope device according to claim 1, wherein the light guide connector comprises an intermediate connector so as to make the second cable attachable to and detachable from the light guide connector.

* * * * *